United States Patent [19]

Halvachs

[11] Patent Number: 4,918,251

[45] Date of Patent: Apr. 17, 1990

[54] PREPARATION OF 2-HALOFLUOROBENZENE

[75] Inventor: Robert Halvachs, Belleville, Ill.

[73] Assignee: Mallinckrodt, Inc., St. Louis, Mo.

[21] Appl. No.: 333,004

[22] Filed: Apr. 4, 1989

[51] Int. Cl.$^4$ .................. C07C 17/24; C07C 21/24
[52] U.S. Cl. ................................... 570/143
[58] Field of Search ........................ 570/143

[56] References Cited

U.S. PATENT DOCUMENTS

| | | | |
|---|---|---|---|
| 2,861,984 | 11/1958 | Gordon et al. | 260/141 |
| 3,424,804 | 1/1969 | Tilney-Bassett | 570/143 |

FOREIGN PATENT DOCUMENTS

| | | | |
|---|---|---|---|
| 12576 | 5/1968 | Japan | 570/143 |
| 296748 | 6/1968 | U.S.S.R. | 570/143 |
| 2204313 | 11/1988 | United Kingdom | 570/143 |

OTHER PUBLICATIONS

Pummer et al., Journal of Research of the National Bureau of Standards vol. 62, No. 3, Mar. 1959, Research Paper 2939, pp. 113–117.
Florin et al., Journal of Research of the National Bureau of Standards, vol. 62, No. 3, Mar. 1959, Research Paper 2940, pp. 119–122.
Introduction to Organic Chemistry, (2nd Ed. 1989), pp. 794–795, by Streitweiser and Heathcock.
The Merck Index, 10th Ed. 1983, Windholz, Editor.

*Primary Examiner*—J. E. Evans
*Attorney, Agent, or Firm*—Bernard Rothwell & Brown

[57] ABSTRACT

A process for producing 2-halofluorobenzene from 2,4-dihalofluorobenzenes comprises treating an aqueous slurry of 2,4-dihalofluorobenzene with hydrogen at an elevated temperature in the presence of a transition metal supported on a carbon catalyst. The process produces a mixture including fluorobenzene and 2-halofluorobenzene. The 2-halofluorobenzene can be separated from the mixture by conventional means such as distillation. Optionally, the fluorobenzene also can be recovered.

16 Claims, No Drawings

PREPARATION OF 2-HALOFLUOROBENZENE

FIELD OF THE INVENTION

The present invention relates to a process for synthesizing 2-halofluorobenzene.

BACKGROUND OF THE INVENTION 2-haloaromatic fluoride compounds, such as 2-bromofluorobenzene, are useful as intermediates in making other compounds. For example, 2-bromofluorobenzene is useful as a starting material for the synthesis of 2-fluorophenol, which in turn is useful as an intermediate for several agricultural, pharmaceutical and polymer compounds. Known methods of producing these compounds include the Sandmeyer and Schiemann reactions. For example, using the Sandmeyer reaction, 2-bromofluorobenzene can be produced from 2-fluoroaniline as shown below:

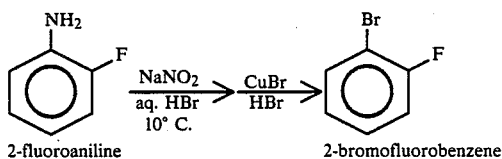

Using the Schiemann reaction, 2-bromofluorobenzene can be produced from 2-bromoaniline as shown below:

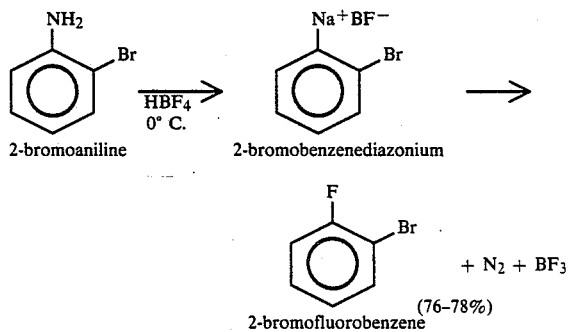

In an alternative version of the Schiemann reaction, hexafluorophosphoric acid is used to produce 2-bromofluoro-benzene from 2-bromoaniline:

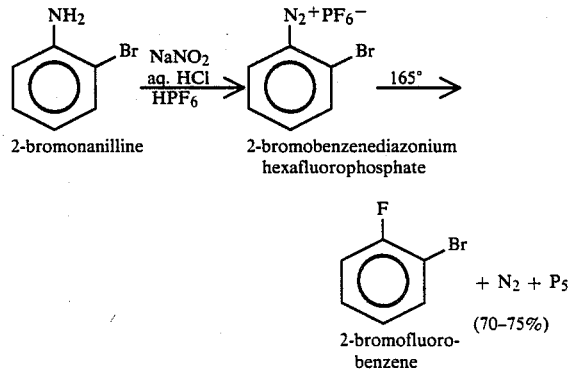

Preparation of haloaromatic compounds using the Sandmeyer and Schiemann reactions is generally discussed by Streitweiser and Heathcock, *Introduction to Organic Chemistry*, (2d. Ed., 1981), pages 794–795. The modified Schiemann reaction for producing 2-bromofluorobenzene using $HPF_6$ is discussed in the same reference at page 796.

There are disadvantages associated with using each of the above reactions for preparing 2-halofluorobenzenes. Some of the starting materials, such as 2-bromoaniline, are relatively expensive, and the reactions produce low yields of products and are fairly hazardous due to the high decomposition temperature of the intermediate diazonium compound. Therefore, a need exists for a process that employs less expensive, more readily available starting materials and utilizes less hazardous reactions to produce 2-halofluorobenzenes.

SUMMARY OF THE INVENTION

The present invention provides a process for the production of 2-halofluorobenzenes from 2,4-dihalofluorobenzenes. The process comprises treating an aqueous solution of di-halofluorobenzene with hydrogen at an elevated temperature in the presence of a transition metal catalyst. The process produces a mixture of fluorobenzene and a 2-halofluorobenzene. The 2-halofluorobenzene can be separated from the mixture by conventional means, such as distillation.

DETAILED DESCRIPTION OF THE PREFERRED EMBODIMENTS

The process of this invention can be used to produce various desired 2-halofluorobenzenes, i.e., 2-bromo-, 2-iodo- or 2-chlorofluorobenzene, from the corresponding 2,4-dihalofluorobenzenes. Preferably, the process is used to prepare 2-bromofluorobenzene from dibromofluorobenzenes.

The starting material for the process of this invention is 2,4-dihalofluorobenzene. The starting compound is used in the form of an aqueous slurry. Generally, the dihalofluorobenzene is present in a total concentration of from about 20% to about 80% by weight. Other dihalofluorobenzene isomers can be present in the starting material without adversely affecting the desired reaction.

For example, if the process is to be employed for the synthesis of 2-bromofluorobenzene, the starting material can be 2,4-dibromofluorobenzene, obtainable commercially or it optionally can comprise a mixture of 2,6-dibromofluorobenzene and 2,4-dibromofluorobenzene, or a mixture of both of the above two compounds with 3,4-dibromofluorobenzene. A mixture of the three isomers conveniently can be used, because they are produced as by-products of a process for the synthesis of 4-bromofluorobenzene. In this process, fluorobenzene is reacted with bromine in the presence of an iron mesh catalyst to produce 4-bromofluorobenzene as well as smaller amounts of 2-bromofluorobenzene and isomeric dibromofluorobenzene by-products. The isomeric dibromofluorobenzene by-products can be recovered and the 2,4-dibromofluorobenzene separated out and used as the starting material in the present invention. The two other dibromofluorobenzenes generally do not react to produce 2-bromofluorobenzene but do not adversely affect the reaction chemistry. The 2,6-dibromofluorobenzene is quite stable, does not react, and can be recovered. The 3,4-dibromofluorobenzene reacts to produce fluorobenzene which also can be recovered.

To reduce the starting material in the process of the present invention, a catalyst is added to the slurry and the material is treated with hydrogen gas while maintaining the temperature at between about 25° to about 75° C., most preferably at about 60° C. Preferably the treatment with hydrogen gas is by forcing at least about 20 psig $H_2$ into the reaction mixture. It is desirable, for practical and economic reasons, to use a pressure of greater than, or equal to, about 20 psig $H_2$ and less than, or equal to about 150 psig $H_2$. The reaction is allowed to proceed until substantially all of the starting material has been hydrogenated. The time needed for hydrogenation to occur will vary, depending upon factors such as the rate at which the hydrogen is forced into the solution and the temperature, which can be used to modify the reaction rate. Lowering the temperature lowers the reaction rate. As an alternative, if it is desired to slow or moderate the reaction, sodium chloride can be added prior to the initiation of hydrogenation. Completion of the reaction can be determined by using a gas-liquid chromatograph equipped with a DB-1701 Megabore column and having helium as the carrier gas. Such chromatographs are known to those of skill in the art and do not comprise part of the present invention.

Preferred catalysts for the process are noble metal catalysts that generally are used in reduction reactions. Typical catalysts of this type are platinum and palladium supported on a carbon base. Most preferably, the catalyst is palladium supported on a carbon base.

Ordinarily, reaction vessels which are designed to accommodate fluorine compounds are used with the present invention. Such fluorine-accommodating vessels are known to those in the art and do not constitute an element of the present invention.

The process of the invention results in a product solution containing both fluorobenzene and 2-halofluorobenzene. The 2-halofluorobenzene portion of the mixture can be recovered using conventional distillation techniques. When the halofluorobenzene is bromofluorobenzene, distillation produces a 2-bromofluorobenzene product which is as much as 99.5% pure. The fluorobenzene produced can also be recovered by conventional distillation techniques and is useful as an intermediate in the synthesis of various pesticides.

In order to illustrate further the nature of this invention, the following example is provided. However, the example is not intended to be limiting but rather is illustrative of the processes embodied by the invention.

EXAMPLE 2,4-dibromofluorobenzene was obtained using the following procedure: Fluorobenzene and an iron mesh catalyst are charged into a reaction vessel which is cooled to about 5° C. The iron mesh catalyst is 40 mesh iron powder. After cooling, approximately stoichiometric amounts of from about 0.5 to 1.0 moles bromine per mole fluorobenzene are slowly added while maintaining the temperature at less than 10° C. After all the bromine has been added, the reaction mixture is stirred for about 40° C. Following cooling to ambient temperature, the reaction products are recovered by distillation. 4-bromofluorobenzene is the major product and is recovered separately from the mixture of isomeric dibromofluorobenzene by-products.

Two hundred grams of this recovered isomeric mixture containing 4% 2,6-dibromofluorobenzene, 20% 3,4-dibromofluorobenzene and 75% 2,4-dibromofluorobenzene were slurried with 200 ml of water in an appropriate reaction vessel. To the slurry were added 20 grams of NaCl and 1 gram of 5% palladium on carbon catalyst. Heat was applied until the reaction mixture attained a temperature of between 60°–65° C. The temperature was maintained at 65° C. Hydrogen gas was forced into the solution at a rate of 20 lbs $H_2$/hr for four hours. A sample of the reacted mixture was subjected to gas-liquid chromatography (GLC) analysis and determined to include 23% fluorobenzene and 68% 2-bromofluorobenzene. The remaining mixture then was fractionally distilled through a 20-plate column with the fluorobenzene collected at 76°–78° C., and the 2-bromofluorobenzene collected at 157°–158° C.

What is claimed is:

1. A process for preparing a 2-halofluorobenzene which comprises:
   treating with hydrogen gas an aqueous slurry of 2,4-dihalofluorobenzene;
   said treatment being carried out in the presence of a transition metal catalyst, wherein said transition metal is selected from the group consisting of platinum and palladium, and at a temperature in the range of about 25° C. to about 75° C.

2. The process of claim 1, further comprising the step of separating the 2-halofluorobenzene from the treated slurry by distillation.

3. The process of claim 2, further comprising the step of adding sodium chloride to said aqueous solution prior to treating said solution with hydrogen gas.

4. The process of claim 3, wherein said treatment with hydrogen gas comprises forcing said hydrogen gas into said aqueous slurry at a pressure of at least about 20 psig $H_2$.

5. The process of claim 4, wherein said hydrogen gas is forced into said aqueous slurry at a pressure from at least about 20 psig $H_2$ to about 150 psig $H_2$.

6. The process of claim 5, wherein said 2,4-dihalofluorobenzene comprises 2,4-dibromofluorobenzene.

7. The process of claim 6, wherein said slurry comprises a mixture of 2,6-dibromofluorobenzene and 2,4-dibromofluorobenzene.

8. The process of claim 6, wherein said slurry comprises a mixture of 2,6-dibromofluorobenzene, 2,4-dibromofluorobenzene and 3,4-dibromofluorobenzene.

9. The process of claim 5 wherein the reaction temperature is about 55° C. to 65° C.

10. The process of claim 5, wherein the transition metal is palladium.

11. A process for preparing 2-bromofluorobenzene which comprises:
   (a) forming an aqueous slurry of a mixture of 2,6-dibromofluorobenzene, 3,4-dibromobenzene and 2,4-dibromobenzene;
   (b) mixing a palladium-on-carbon catalyst with said slurry;
   (c) heating said slurry to about 60° to 65° C., and
   (d) treating said heated slurry with hydrogen gas.

12. The process of claim 11, further comprising recovering said 2-bromofluorobenzene.

13. The process of claim 11, further comprising adding sodium chloride to said mixture prior to heating.

14. The process of claim 1, 5, 11 or 12, further comprising recovering fluorobenzene from said treated slurry.

15. The process of claim 11, wherein said hydrogen gas treatment comprises forcing said hydrogen gas into said slurry by applying a pressure of at least about 20 psig $H_2$.

16. The process of claim 15, wherein said forcing pressure is from about 20 psig to about 150 psig $H_2$.

* * * * *

UNITED STATES PATENT AND TRADEMARK OFFICE
CERTIFICATE OF CORRECTION

PATENT NO. : 4,918,251

DATED : April 17, 1990

INVENTOR(S) : Robert Halvachs

It is certified that error appears in the above-identified patent and that said Letters Patent is hereby corrected as shown below:

Col. 1, line 56, "2-bromonanilline" should be --2-bromoaniline--.

Signed and Sealed this

Second Day of July, 1991

Attest:

HARRY F. MANBECK, JR.

Attesting Officer

Commissioner of Patents and Trademarks